United States Patent
Song et al.

(10) Patent No.: US 12,414,976 B2
(45) Date of Patent: Sep. 16, 2025

(54) PHARMACEUTICAL COMPOSITION FOR PREVENTING HAIR LOSS OR PROMOTING HAIR GROWTH, COMPRISING GINSENOSIDE RG4 OR MIXTURE (Rgx 365) OF GINSENOSIDES Rg2, Rg4, Rg6, AND Rh1 AS ACTIVE INGREDIENT

(71) Applicant: AREZ CO., LTD., Daejeon (KR)

(72) Inventors: Gyu Yong Song, Daejeon (KR); Jee Hyun Lee, Daejeon (KR)

(73) Assignee: AREZ CO., LTD., Daejeon (KR)

( * ) Notice: Subject to any disclaimer, the term of this patent is extended or adjusted under 35 U.S.C. 154(b) by 789 days.

(21) Appl. No.: 17/622,541

(22) PCT Filed: Jun. 23, 2020

(86) PCT No.: PCT/KR2020/008159
§ 371 (c)(1),
(2) Date: Dec. 23, 2021

(87) PCT Pub. No.: WO2020/262933
PCT Pub. Date: Dec. 30, 2020

(65) Prior Publication Data
US 2022/0354915 A1 Nov. 10, 2022

(30) Foreign Application Priority Data
Jun. 25, 2019 (KR) .................. 10-2019-0075487

(51) Int. Cl.
| | | |
|---|---|---|
| A61K 36/258 | (2006.01) | |
| A23L 33/105 | (2016.01) | |
| A61K 8/60 | (2006.01) | |
| A61P 17/14 | (2006.01) | |

(52) U.S. Cl.
CPC .......... *A61K 36/258* (2013.01); *A23L 33/105* (2016.08); *A61K 8/60* (2013.01); *A61P 17/14* (2018.01)

(58) Field of Classification Search
CPC ....... A61K 36/25; A61K 36/258; A61K 17/14
See application file for complete search history.

(56) References Cited

U.S. PATENT DOCUMENTS

2015/0297727 A1* 10/2015 Zhan ............... C07J 17/005
514/26
2016/0263169 A1* 9/2016 Kim ................ A61K 36/78

FOREIGN PATENT DOCUMENTS

| CN | 102302420 A | 1/2012 |
|---|---|---|
| CN | 105250152 A | 1/2016 |
| KR | 10-2014-0058923 A | 5/2014 |
| KR | 10-2017-0094632 A | 8/2017 |
| KR | 10-1783295 B1 | 9/2017 |
| KR | 10-1819418 B1 | 1/2018 |
| KR | 10-2018-0115610 A | 10/2018 |

OTHER PUBLICATIONS

Pubchem: ginsenoside rg4; 1 pgs.*
Yu et al. Chem Pharm Bull, 50(2), 175-175.*
Choi et al., Int J Mol Sci, 2018, 1-13.*
International Search Report issued for International Application No. PCT/KR2020/008159 on Sep. 22, 2020, 4 pages.
Lee, W. et al. Inhibitory effects of protopanaxatriol type ginsenoside fraction (Rgx365) on particulate matter-induced pulmonary injury, Journal of Toxicology and Environmental Health. Part A. 2019 (Electronic publication on Mar. 27, 2019), vol. 82. 14 Pages.
Choi, B. Y. Hair-Growth Potential of Ginseng and Its Major Metabolites: A Review on Its Molecular Mechanisms. Int. J. Mol. Sci. Sep. 11, 2018, vol. 19, document No. 2703, pp. 1-13.
Andl, T. et al., WNT signals are required for the initiation of hair follicle development, Dev Cell., (2002), 2(5), 643-653.
De Lacharriere. O. et al., Hair diameter diversity: a clinical sign reflecting the follicle miniaturization, Arch Dermatol., (2001), 137(5), 641-646.
Higgins, C. A. et al., Modelling the hair follicle dermal papilla using spheroid cell cultures, Exp Dermatol., (2010), 19(6), 546-548.
Higgins, C. A. et al., Microenvironmental reprogramming by three-dimensional culture enables dermal papilla cells to induce de novo human hair-follicle growth, Proc Natl Acad Sci USA., (2013), 110(49), 19679-19688.
Jahoda, C. A., Cellular and developmental aspects of androgenetic alopecia, Exp Dermatol., (1998), 7(5), 235-248.
Kang, B. M. et al., Sphere formation increases the ability of cultured human dermal papilla cells to induce hair follicles from mouse epidermal cells in a reconstitution assay, J Invest Dermatol., (2012), 132(1), 237-239.
Kim, Y. S. et al., Differential expression of protein kinase C subtypes during ginsenoside Rh2-Induced apoptosis in SK-N-BE(2) and C6Bu-1 cells, Arch Pharm Res., (2000), 23(5), 518-524.

(Continued)

*Primary Examiner* — Kyle A Purdy
(74) *Attorney, Agent, or Firm* — ROTHWELL, FIGG, ERNST & MANBECK, P.C.

(57) ABSTRACT

The present invention relates to a composition for preventing hair loss or promoting hair growth, comprising ginsenoside Rg4 or a mixture of ginsenosides Rg2, Rg4, Rg6, and Rh1 as an active ingredient. Treatment with ginsenoside Rg4 or the mixture of ginsenosides Rg2, Rg4, Rg6, and Rh1 in human hair follicle dermal papilla cells exhibits a desirable effect of forming three-dimensional spheres capable of inducing hair follicle formation and growth and increasing the size thereof, exhibits a desirable effect of activating Wnt/β-catenin signaling, which is important for hair follicle cell activation and regeneration, and exhibits a desirable effect of increasing the expression levels of ALPL, VCAN, BMP2, and FGF7 genes, which are important for hair follicle formation and growth. Thus, ginsenoside Rg4 or the mixture of ginsenosides Rg2, Rg4, Rg6, and Rh1 can be usefully utilized as a composition for preventing hair loss and promoting hair growth.

9 Claims, 6 Drawing Sheets

(56) References Cited

OTHER PUBLICATIONS

Kishimoto, J. et al., Wnt signaling maintains the hair-inducing activity of the dermal papilla, Genes Dev., (2000), 14(10). 1181-1185.
Park, G. H. et al., Red ginseng extract promotes the hair growth in cultured human hair follicles, J Med Food., (2015), 18(3), 354-362.
Shibata, S., Chemistry and cancer preventing activities of ginseng saponins and some related triterpenoid compounds, J Korean Med Sci., (2001), 16(suppl), S28-37.
Tachikawa, E. et al., In vitro inhibition of adrenal catecholamine secretion by steroidal metabolites of ginseng saponins, Biochem Pharmacol., (2003), 66(11), 2213-2221.
Topouzi, H. et al., Methods for the isolation and 3D culture of dermal papilla cells from human hair follicles, Exp Dermatol., (2017), 26(6), 491-496.
Tsai, S. C. et al., Stimulation of the secretion of luteinizing hormone by ginsenoside-Rb1 in male rats, Chin J Physiol., (2003), 46(1), 1-7.
Whiting, D. A., Possible mechanisms of miniaturization during androgenetic alopecia or pattern hair loss, J Am Acad Dermatol., (2001), 45(3 Suppl), S81-S86.
European Search Report issued for European Patent Application No. 20 831 024.3 on Jul. 13, 2023, 8 pages.

* cited by examiner

PHARMACEUTICAL COMPOSITION FOR PREVENTING HAIR LOSS OR PROMOTING HAIR GROWTH, COMPRISING GINSENOSIDE RG4 OR MIXTURE (Rgx 365) OF GINSENOSIDES Rg2, Rg4, Rg6, AND Rh1 AS ACTIVE INGREDIENT

CROSS REFERENCE TO RELATED APPLICATION(S)

This application is a 35 U.S.C. 371 National Phase Entry Application from PCT/KR2020/008159, filed on Jun. 23, 2020 and designating the United States, which claims priority based on Korean Patent Application No. 10-2019-0075487 filed on Jun. 25, 2019, all of the disclosures of which are incorporated herein by reference in their entirety.

TECHNICAL FIELD

The present disclosure relates to a pharmaceutical composition comprising ginsenoside Rg4 or a mixture (Rgx 365) of ginsenosides Rg2, Rg4, Rg6, and Rh1 as an active ingredient for preventing hair loss or promoting hair growth.

BACKGROUND ART

As many as 100,000-150,000 hairs are counted on human scalps, with their respective growth cycles repeating. The hair growth cycle has three stages: the anagen stage in which hairs most actively grow; the catagen stage in which hairs start to regress; and the telogen stage in which hairs cease to grow and enter a rest. Hairs amounting to about 15% of the total number of scalp hairs are in the telogen and catagen stages and people typically lose 50 to 100 hairs a day while new hair is growing at the same time.

In general, hair loss refers to a state in which there is no hair in the area where hair should normally exist because abnormally shedding hairs are increasing in number as the proportion of hairs in the anagen stage becomes small while the proportion of hairs in the catagen or telogen state decreases. Previously, hair loss was recognized as a series of aging phenomena, but recently, excessive stress, poor blood circulation of the scalp, excessive androgen secretion, seborrheic dermatitis, genetic factors, nutritional deficiencies, iron deficiencies, drugs, and hypothyroidism are considered to be the causes.

Drugs approved for promotion of hair growth by the FDA (Food and Drug Administration) include minoxidil, finasteride, Propecia, etc. However, widely used minoxidil-containing hair growth agents, although approved as over-the-counter drugs by the FDA, cannot be administered to women and cause adverse effects such as skin irritation, itchiness, redness, aggravation of hair loss, etc. Finasteride formulations should be administered with care according to the reports that they may cause fetal deformity in pregnant women and persons who take finasteride for a long period of time might suffer from adverse effects including hypoactive sexual desire, erectile dysfunction, disturbance of ejaculation, and so on. Propecia formulations may lead to feminization of men and has the problem that there is a high risk of giving birth to deformed babies in women of childbearing age. Therefore, there is a need for the development of a novel material that is safe even upon use for a long period of time without adverse effects and which exhibits the effect of preventing hair loss and promoting hair growth by improving scalp conditions.

Ginsenosides, which are a compound word of ginseng and glycosides, are known to have distinct chemical structures and pharmaceutical efficacies discriminated from saponins found in different plants. The ginsenosides are neutral gycosides in which glucose, arabinose, xylose, rhamnose, and so on are bonded to the triterpenoid dammarane skeleton. As many as 30 chemical structures are currently known, with division into 19 protopanaxadiols (PPD), 10 protopanaxatriols (PPT), and 1 oleanane.

Fresh ginseng or white ginseng include Rg1, Re, Rf, Rh1, Rb1, Rb2, Rc, and Rd as main ginsenosides which account for 80-90% of the total amount of ginsenosides therein. Rare ginsenosides are produced as the main ginsenosides are subjected to partial sugar release therefrom or to dehydration and found in a trace amount in a water or alcohol extract of ginseng.

The pharmaceutical activities of ginsenosides are, for the most part, attributed to rare ginsenosides and among them, immunopotentiation, anti-inflammation, anti-allergy, anti-cancer, hypotension, anti-cholesterol, anti-thrombosis, anti-aging, anti-oxidation, brain activity promotion, and skin care are known as main efficacies (Kim, Y. S. et al., Arch Pharm Res., 23(5), 518-524, 2000; Shibata, S., J Korean Med Sci., 16(suppl), S28-37, 2001; Tachikawa, E. et al., Biochem Pharmacol., 66(11), 2213-2221, 2003; Tsai, S. C. et al., Chin J Physiol., 46(1), 1-7, 2003).

As related art documents pertaining to compositions comprising ginsenoside Rg4 or a mixture of ginsenosides Rg2, Rg4, Rg6, and Rh1 as active ingredient for preventing hair loss or promoting hair growth, Korean Patent No. 10-2017-0094632 A discloses a shampoo comprising a ginsenoside Rg2-enriched red ginseng extract for prevention of hair loss, Korean Patent No. 10-1819418 discloses a cosmetic composition comprising a complex of ginsenosides Rh1, Rb1, Rc, and Rg3 for promoting hair growth and preventing hair loss, Korean Patent No. 10-2014-0058923 A discloses a cosmetic composition comprising ginsenosides Rg1 and Re for promoting hair growth or preventing hair loss, and the document [Park, G. H. et al., J Med Food., 18(3), 354-362, 2015] discloses a promotive effect of a red ginseng extract on hair growth. However, no previous reports disclose that ginsenoside Rg4 or a mixture of ginsenosides Rg2, Rg4, Rg6, and Rh1 has an effect of preventing hair loss or promoting hair growth as in the present disclosure.

Accordingly, leading to the present disclosure, the research, conducted by the present inventors, into ginsenosides, resulted in the finding that ginsenoside Rg4 or a mixture of ginsenosides Rg2, Rg4, Rg6, and Rh1 is particularly selective for prevention of hair loss or promotion of hair growth, compared to single ginsenosides Rg2, Rg6, and Rh1, a ginseng extract, and a red ginseng extract.

DISCLOSURE OF INVENTION

Technical Problem

An aspect of the present disclosure is to provide a pharmaceutical composition, a cosmetic composition, and a health functional food, each comprising ginsenoside Rg4 or a mixture (Rgx 365) of ginsenosides Rg2, Rg4, Rg6, and Rh1 as an active ingredient for preventing hair loss or promoting hair growth.

Solution to Problem

The present disclosure relates to a pharmaceutical composition comprising ginsenoside Rg4 or a mixture of ginsenosides Rg2, Rg4, Rg6, and Rh1 as an active ingredient for preventing hair loss or promoting hair growth.

The mixture contains 35-45% by weight of ginsenoside Rg2, 30-40% by weight of ginsenoside Rg4, 10-20% by weight of ginsenoside Rg6, and 1-5% by weight of ginsenoside Rh1. In this regard, the ginsenosides may be individually mixed according to the % by weight set therefor, or any typical method that can prepare the mixture is included within the present disclosure, without limitations. The mixture may be preferably prepared by mixing ginsenoside Re with 130-160 parts by weight of distilled water and treating the mixture for 4-6 hours in a temperature range of 110-140° C. at a pressure of 0.11-0.16 MPa, followed by column separation.

The pharmaceutical composition may be formulated into suitable forms with pharmaceutically acceptable carriers. The expression "pharmaceutically acceptable" means that the composition is physiologically acceptable and is non-toxic without causing allergic or other similar adverse reactions, such as gastroenteric trouble or dizziness, when administered to a human. In addition, the composition may be administered orally, topically, and transdermally and may be formulated into any dosage form, for example, oral dosage forms such as a pulvis, a granule, a tablet, a capsule, a suspension, an emulsion, a syrup, an aerosol, and so on, agents for external use, suppositories, and sterile injections.

The pharmaceutical composition may be used as a topical skin formulation selected from the group consisting of a cream, a gel, an ointment, a hard plaster, a lotion, a liquid, an emulsion, a powder, and a spray.

The term "topical skin formulation" refers to any formulation that can be applied to skin from the outside and the composition may be formulated with a cosmetically or dermatologically acceptable medium or base.

For the topical skin formulation in the form of cream or gel, animal oil, plant oil, wax, paraffin, starch, tragacanth, cellulose derivative, polyethylene, glycol, silicone, bentonite, silica, talc or zinc oxide, etc. may be used as a carrier ingredient.

For the topical skin formulation in the form of powder or spray, lactose, talc, silica, aluminum hydroxide, calcium silicate, or polyamide powder may be used as a carrier, and particularly in case of spray, a propellant such as chlorofluorohydrocarbon, propane/butane, or dimethyl ether may be additionally contained.

As a carrier for the formulation in the form of a solution or an emulsion, a solvent, a solvation agent, or an emulsifier may be used and examples of the carrier include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol or sorbitan fatty acid ester.

The topical skin formulation may comprise an agent which increases percutaneous absorption such as, for example and in a non-limiting sense, dimethyl sulfoxide, dimethyl acetamide, dimethyl formamide, a surfactant, azone, alcohol, acetone, propyleneglycol or polyethylene glycol, among others. The application frequency of the composition may significantly vary, depending on the needs of each subject, an application frequency range from 10 times a month up to 10 times a day being suggested, preferably from four times a week up to four times a day, more preferably from three times a week up to three times a day, even more preferably one or two times a day.

The pharmaceutical composition of the present disclosure may be administered in a pharmaceutically effective amount. As used herein, the term "administration" refers to introduction of a predetermined substance into a subject by a suitable method. So long as it can reach a target tissue, any general administration route may be taken to administer the composition. For example, the composition may be administered orally, intrarectally, intravenously, intramuscularly, subcutaneously, intraperitoneally, or topically, but with no limitations thereto.

As used herein, the term "subject" is intended to encompass all animals including humans, rats, mice, livestock, etc., with preference for mammals including humans.

As used herein, the term "pharmaceutically effective amount" refers to an amount sufficient to treat a disease at a reasonable benefit/risk ratio applicable to medical treatment, without causing an adverse effect. The effective dosage level of the composition may be determined by a person skilled in the art, depending on various factors including patient's sex, age, body weight, and health state, the kinds of disease, the severity of disease, the activity of drug, sensitivity to drug, administration mode, administration time, administration route, excretion rate, the duration of treatment, and drugs formulated or used simultaneously, and other factors known in the medical field. Preferably, the ginsenoside of the present disclosure may be administered at a dose of 0.0001 to 100 mg/kg of body weight and more preferably at a dose of 0.001 to 100 mg/kg of body weight a day, based on the solid content thereof. The composition may be administered in a single or multiple dosage form a day.

According to another aspect thereof, the present disclosure pertains to a cosmetic composition comprising ginsenoside Rg4 or a mixture of ginsenosides Rg2, Rg4, Rg6, and Rh1 as an active ingredient for preventing hair loss or promoting hair growth.

The cosmetic composition may be formulated into any form that is typically used in the art and may be prepared into a formulation selected from the group consisting of a solution, an emulsion, a suspension, a paste, a gel, a powder, a skin lotion, a lotion, a cream, an essence, a spray, a shampoo, a conditioner, and a soap, but with no limitations thereto.

In addition, the cosmetic composition may comprise any ingredient that is typically allowed for cosmetics in addition to the active ingredient. For example, general auxiliary agents, such as emulsifiers, thickeners, emollients, surfactants, lubricants, alcohols, water-soluble polymers, gelling agents, stabilizers, vitamins, inorganic salts, and fragrances, and excipients may be contained. According to the formulation type or use purpose, selection may be made of the amounts of the ingredients within a range that does not degrade the characteristic effect of the cosmetic.

The cosmetically acceptable carrier available for the cosmetic composition of the present disclosure varies depending on formulations of the cosmetic composition.

As a carrier for the formulation in the form of a solution or an emulsion, a solvent, a solvation agent, or an emulsifier may be used and examples of the carrier include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol or sorbitan fatty acid ester.

For the formulation in the form of a suspension, a liquid-phase diluent such as water, ethanol, or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, or tragacanth may be available as a carrier.

For the formulation in the form of paste, cream or gel, animal oil, plant oil, wax, paraffin, starch, tragacanth, cellulose derivative, polyethylene, glycol, silicone, bentonite, silica, talc or zinc oxide, etc. may be used as a carrier ingredient.

For the formulation in the form of powder or spray, lactose, talc, silica, aluminum hydroxide, calcium silicate, or polyamide powder may be used as a carrier, and particularly in case of spray, a propellant such as chlorofluorohydrocarbons, propane/butane or dimethyl ether may be additionally contained.

The cosmetic composition comprising ginsenoside Rg4 or a mixture of ginsenosides Rg2, Rg4, Rg6, and Rh1 may be used every day and may be used for an undetermined period of time, and preferably, its usage, number of use, and duration may be adjusted according to the age, skin condition, or skin type of the user, concentrations of ginsenoside Rg4 or a mixture of ginsenosides Rg2, Rg4, Rg6, and Rh1.

Another aspect of the present disclosure is concerned with a health functional food comprising ginsenoside Rg4 or a mixture of ginsenosides Rg2, Rg4, Rg6, and Rh1 as an active ingredient for preventing hair loss or promoting hair growth.

As used herein, the term "health functional food" refers to a food prepared or processed from raw material or ingredient having useful functionality and is intended to encompass, for example, health aid foods, functional foods, nutrients, food supplements, and so on.

The ginsenoside may be added preferably in an amount of 0.001% by weight to 50% by weight, more preferably in an amount of 0.001% by weight to 30% by weight, and most preferably in an amount of 0.001% by weight to 10% by weight, based on the total weight of the health functional food.

The health functional food of the present disclosure may be in the form of a tablet, a capsule, a pill, and a liquid. Examples of the food to which the ginsenoside Rg4 or the mixture of ginsenosides Rg2, Rg4, Rg6, and Rh1 can be added include various foods, beverages, gum, teas, vitamin complexes, etc.

Advantageous Effects of Invention

The present disclosure relates to a composition comprising ginsenoside Rg4 or a mixture of ginsenosides Rg2, Rg4, Rg6, and Rh1 as an active ingredient for preventing hair loss or promoting hair growth. The ginsenoside Rg4 or the mixture of ginsenosides Rg2, Rg4, Rg6, and Rh1, when applied to human hair follicle dermal papilla cells, exhibits excellent effects of increasing the formation and size of three-dimensional spheroids able to induce follicle formation and growth, activating the Wnt/β-catenin signaling pathway important for follicle cell activation and regeneration, and upregulating the expression of ALPL, VCAN, BMP2, and FGF7 genes responsible for follicle formation and growth, thus finding advantageous applications in a composition for preventing hair loss and promoting hair growth.

BEST MODE FOR CARRYING OUT THE INVENTION

Hereinafter, the present disclosure will be described in detail with reference to exemplary embodiments. However, these exemplary embodiments are for specifically illustrating the present disclosure and the scope of the present disclosure is not limited to these exemplary embodiments.

Example 1: Preparation of Ginsenoside Rg4

With reference to Korean Patent No. 10-1783295, ginsenoside Rg4 was prepared from ginsenoside Re.

Example 2: Preparation of Mixture (Rgx 365) of Ginsenosides Rg2, Rg4, Rg6, and Rh1

With reference to Korean Patent Application No. 10-2019-0041458, a mixture (Rgx 365) of ginsenosides Rg2, Rg4, Rg6, and Rh1 was prepared.

Experimental Example 1: Cell Culture

With reference to the documents [Topouzi, H. et al., Exp Dermatol., 26(6), 491-496, 2017; Higgins, C. A. et al., Proc Natl Acad Sci USA., 110(49), 19679-19688, 2013; Higgins, C. A. et al., Exp Dermatol., 19(6), 546-548, 2010], human hair follicle dermal papilla (HDP) cells were incubated in a general 2D monolayer culture manner and in a 3D spheroid culture manner as in the actual human follicle structure.

First, for 2D monolayer culture, human hair follicle dermal papilla cells were cultured in a mesenchymal stem cell medium (MSCM) (Innoprot, Bizakaia, Spain) supplemented with 5% fetal bovine serum (FBS, Thermo Fisher Scientific, Inc., Waltham, MA, USA) in an incubator maintaining the condition of 37° C. and 5% $CO_2$.

Next, for 3D spheroid culture, human hair follicle dermal papilla cells were cultured in a plate (round-bottom ultra-low attachment microplate, Corning, NY, USA) containing the stem cell medium supplemented with 5% fetal bovine serum at 37° C. under a 5% $CO_2$ atmosphere.

HEK293 cells were cultured in DMEM (Dulbecco's Modified Eagle's Medium, Thermo Fisher Scientific, Inc.) supplemented with 10% fetal bovine serum, penicillin (50 U/ml), and streptomycin (50 U/ml) under the condition of 37° C. and 5% $CO_2$.

Experimental Example 2: Assay for Cell Viability

Cell viability of the human hair follicle dermal papilla cells treated according to the Examples of the present disclosure was examined by WST-1 assay (WST-1 assay kit, water soluble tetrazolium salt, Daeil Lab Service Co. Ltd, Korea).

First, the human hair follicle dermal papilla cells cultured in a 2D or 3D manner in Experimental Example 1 were seeded at a density of $1 \times 10^4$ cells/well into 96-well plates (96-well round-bottom ultra-low attachment microplates) and incubated at 37° C. for 24 hours in a 5% $CO_2$ atmosphere. After removal of the medium, the cells were cultured for 48 hours in media containing various concentrations of Example 1 or 2. Then, 10 μl of the WST-1 solution was added to the culture and incubated for 30 min before reading absorbance at 450 nm on an iMark microplate reader (Bio-Rad Laboratories, Hercules, CA, USA). For reliability, experiments were conducted in triplicate. Experiment results are depicted in FIGS. 1 and 2.

Figure 1:
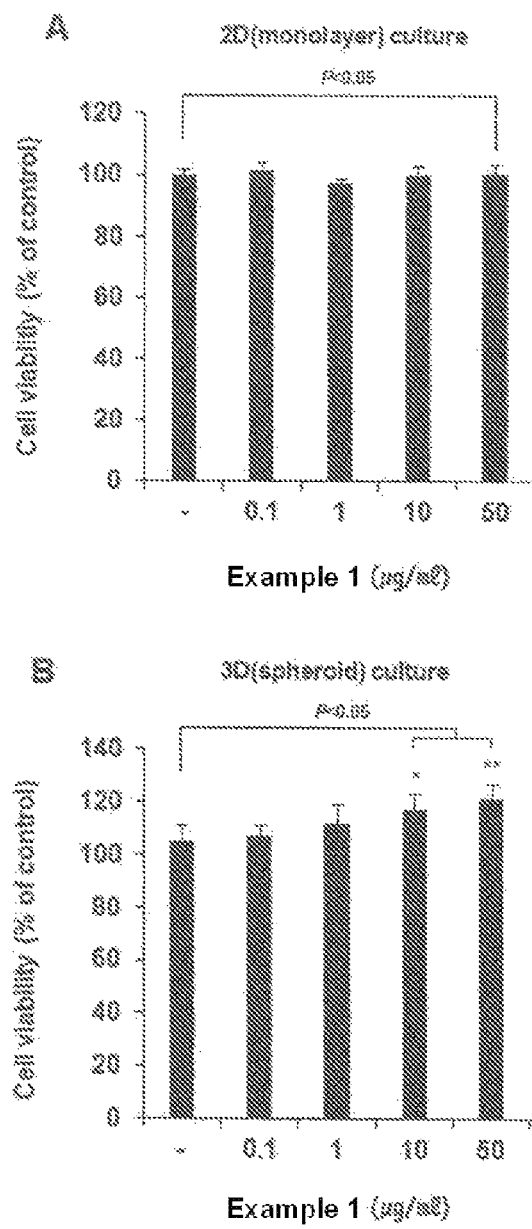
FIGS. 1A and 1B show assay results for cell viability of human hair follicle dermal papilla cells cultured in a 2D (monolayer) and a 3D (spheroid) manner according to treatment concentrations of Example 1 of the present disclosure.
Figure 2:
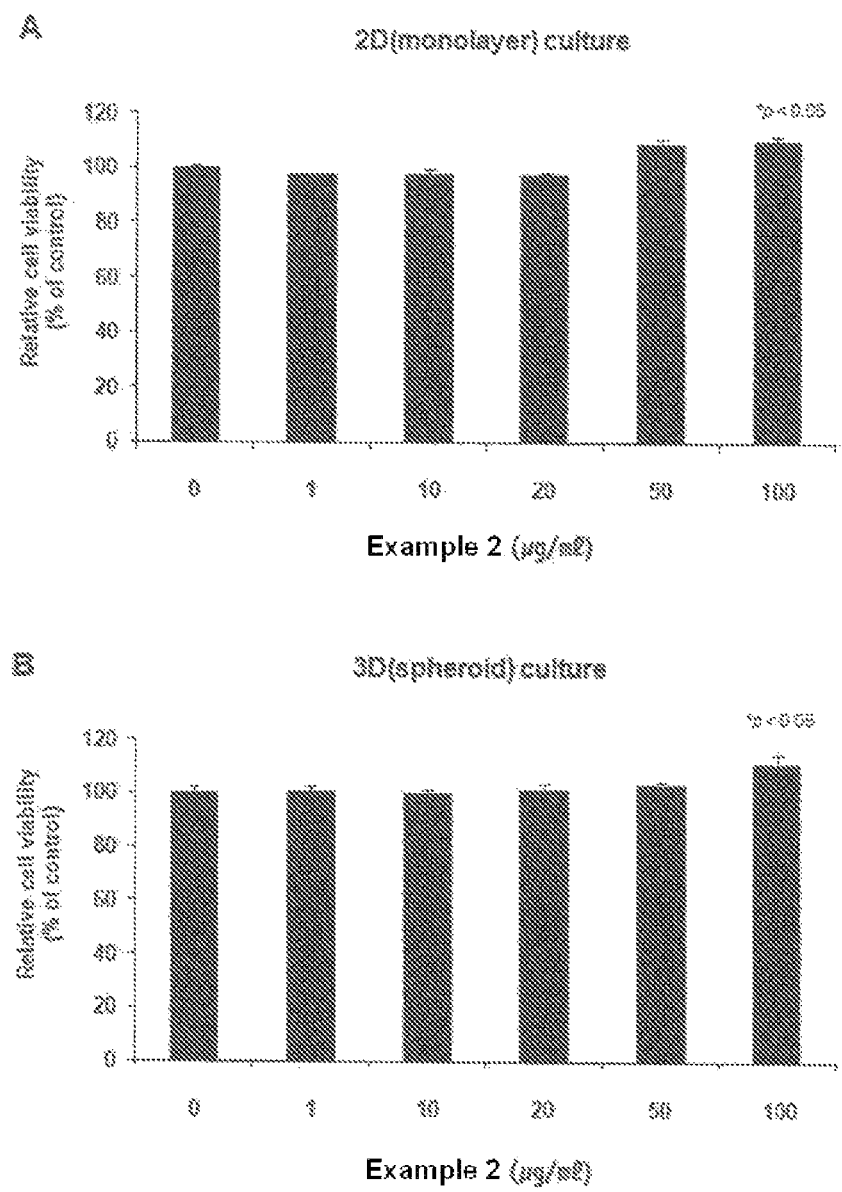
FIGS. 2A and 2B show assay results for cell viability of human hair follicle dermal papilla cells cultured in a 2D (monolayer) and a 3D (spheroid) manner according to treatment concentrations of Example 2 (Rgx 365) of the present disclosure.

With reference to FIGS. 1 and 2, Examples 1 and 2 exhibited the same cell viability of the 2D or 3D cultured human hair follicle dermal papilla cells as in the non-treated group irrespective of the concentrations thereof, which demonstrates that Examples 1 and 2 are materials free of cytotoxicity.

Experimental Example 3: Effect of Hair Loss Prevention and Hair Growth Promotion Experimental Example 3-1. Formation of 3D Spheroid Referring to the document [Higgins, C. A. et al., Exp Dermatol., 19(6), 546-548, 2010; Higgins, C. A. et al., Proc Natl Acad Sci USA., 110(49), 19679-19688, 2013; Kang, B. M. et al., J Invest Dermatol., 132(1), 237-239, 2012], a 3D spheroid culture of human hair follicle dermal papilla cells is reported to induce better formation and growth of hair follicles, compared to a 2D culture of human hair follicle dermal papilla cells. In addition, the document [Whiting, D. A., J Am Acad Dermatol., 45(3 Suppl), S81-S86, 2001; de Lacharriere, O. et al., Arch Dermatol., 137(5), 641-646, 2001; Jahoda, C. A., Exp Dermatol., 7(5), 235-248, 1998] reports that a decrease in the size of dermal papilla may cause follicle miniaturization in patients with hair loss. The Examples of the present disclosure were examined for effects of preventing hair loss and promoting hair growth by monitoring the formation and size of 3D spheroids after application to the 3D spheroid culture of Experimental Example 1.

First, the formation and size change of 3D spheroids of human hair follicle dermal papilla cells were observed. In this regard, the 3D spheroid culture of cells in Experimental Example 1 was seeded at a density of $5 \times 10^4$ cells/well into 96-well plates (96-well round-bottom ultra-low attachment microplates) and incubated for 48 hours with predetermined concentrations of Examples 1 and 2 and Comparative Example 1 (ginsenoside Rg2). Thereafter, the human dermal papilla cells were observed under a phase-contrast microscope to see whether the cells formed 3D spheroids and to measure sizes of the spheroids. The results are given in FIGS. 3 and 4.

Figure 3:
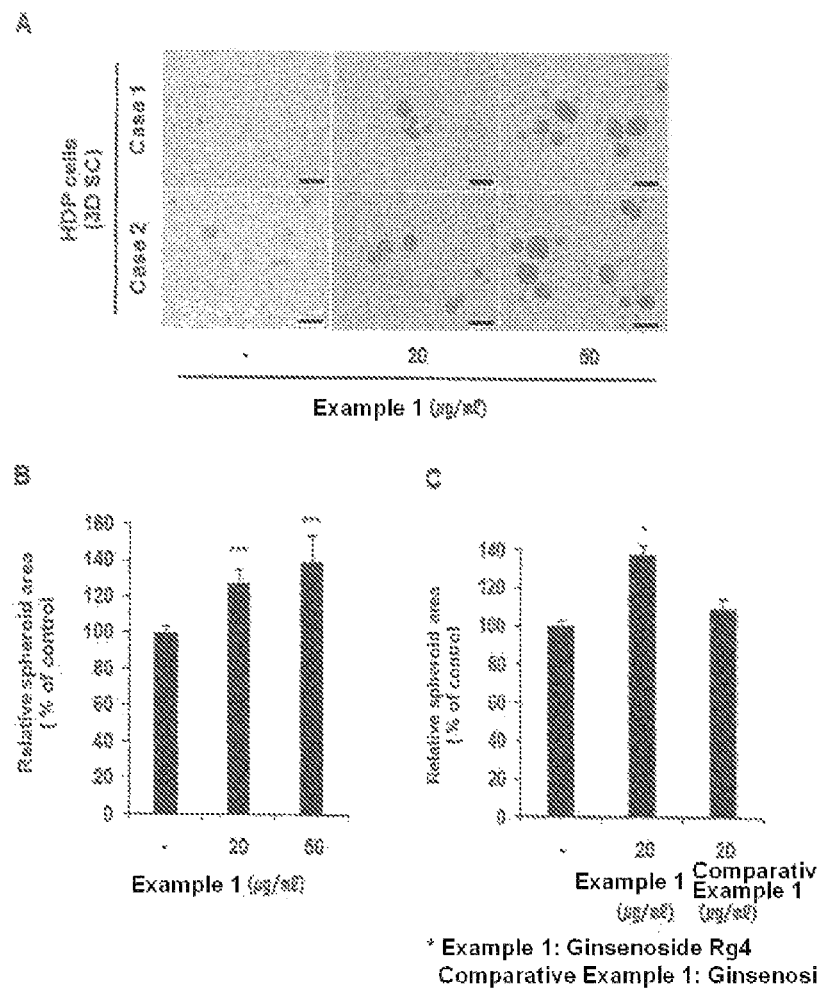
FIGS. 3A, 3B, and 3C shows the formation of 3D spheroids of human hair follicle dermal papilla cells cultured in a 3D pattern according to the treatment of Example 1 (ginsenoside Rg4) of the present disclosure or Comparative Example 1 (ginsenoside Rg2) in contrast-phase microscope images and graphs depicted on the basis of digitized data.
Figure 4:
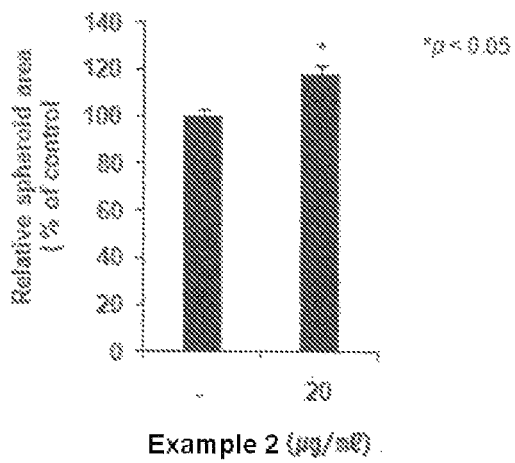
FIG. 4 shows assay results for the sizes of 3D spheroid of the human hair follicle dermal papilla cells cultured in a 3D pattern in the presence or absence of Example 2 (Rgx 365) of the present disclosure.

With reference to FIGS. 3 and 4, the 3D culture of human hair follicle dermal papilla cells treated with Example 1 or 2 was observed to increase the number and size of 3D spheroids in a concentration-dependent manner, as opposed to the non-treated group.

Particularly turning to FIG. 3C, when applied to the 3D culture of human hair follicle dermal papilla cells, ginsenoside Rg4 of Example 1 increased the number and size of the 3D spheroids two to three folds, compared to ginsenoside Rg2 of Comparative Example 1, which implies that ginsenoside Rg4 of Example 1 is more selective for the effect of preventing hair loss and promoting hair growth.

It was understood from the result that ginsenoside Rg4 or a mixture (Rgx 365) of ginsenosides Rg2, Rg4, Rg6, and Rh1 is superb in terms of inductive property for hair growth promotion and hair loss prevention.

Experimental Example 3-2. Activation of Wnt/β-Catenin Signaling Pathway

According to the document [Andl, T. et al., Dev Cell., 2(5), 643-653, 2002; Kishimoto, J. et al., Genes 8 Dev., 14(10), 1181-1185, 2000], it is reported that the Wnt/β-catenin signaling pathway plays an important role in promoting the formation of hair follicles and maintaining and activating genes expressed during the anagen stage of the hair cycle. Thus, Wnt/β-catenin is in a very important position in activating and regenerating hair follicle cells. In this regard, when treated with the Example of the present disclosure, the cells cultured in Experimental Example 1 were examined for Wnt/β-catenin signaling activation, which leads to the effect of preventing hair loss and promoting hair growth.

Whether the Wnt/β-catenin signaling is activated or not was determined using a TCF/LEF luciferase reporter plasmid (TOPFlash, Merck-Millipore, Darmstadt, Germany) designed to specifically react with the transcription factor TCF/LEF activated by β-catenin, and a reporter plasmid having a mutation caused in the promoter thereof (FOP-Flash, Merck-Millipore, Darmstadt, Germany).

First, the TCF/LEF luciferase reporter plasmid (TOPFlash (TCF/LEF-wt) or FOPFlash (TCF/LEF-mut)) and a β-galactosidase plasmid were transfected into the HEK293 cells cultured in Experimental Example 1 with the aid of Lipofectamine 3000 (Invitrogen, Thermo Fisher Scientific, Inc.). After being incubated with 20 μg/ml of Example 1 for 24 hours, the transfected cells were lysed with a passive lysis buffer (Promega, Madison, WI, USA). The cell lysate thus formed was added with D-luciferin and measured for luciferase activity by Glomax 96 Microplate Luminometer (Turner Biosystem, Sunnyvale, CA, USA). β-Galactosidase activity was measured with the aid of Luminescent β-galactosidase Detection Kit II (Clontech Laboratories Inc., USA). On the basis of the data, luciferase activity values were derived, and are depicted in FIG. 5A. For reliability, experiments were conducted in triplicate.

Next, in order to confirm the luciferase activity results, mRNA analysis was performed on β-catenin, WNT5A, and LEF1, which are involved in the Wnt/β-catenin signaling. First, a 3D spheroid culture of human hair follicle dermal papilla cells was treated with Example 1 (20 µg/ml) for 48 hours, followed by RNA extraction with a TRIzol solution (Invitrogen, Thermo Fisher Scientific). From 2 µg of the RNA extract, cDNA was synthesized in the presence of M-MLV reverse transcriptase. The synthesized cDNA was mixed with HOT FIREPol EvaGreen qPCR Mix Plus solution (Solis BioDyne, Tartu, Estonia) and each of primer sets for the Wnt/β-catenin target genes β-catenin, WNT5A, and LEF1 and subjected to Step OnePlus Real-Time PCR (Applied Biosystems; Thermo Fisher Scientific). Relative to the expression of β-actin housekeeping gene, an expression level of each gene was derived. Analysis results of mRNA expressions are depicted in FIGS. 5B to 5D.

Figure 5:
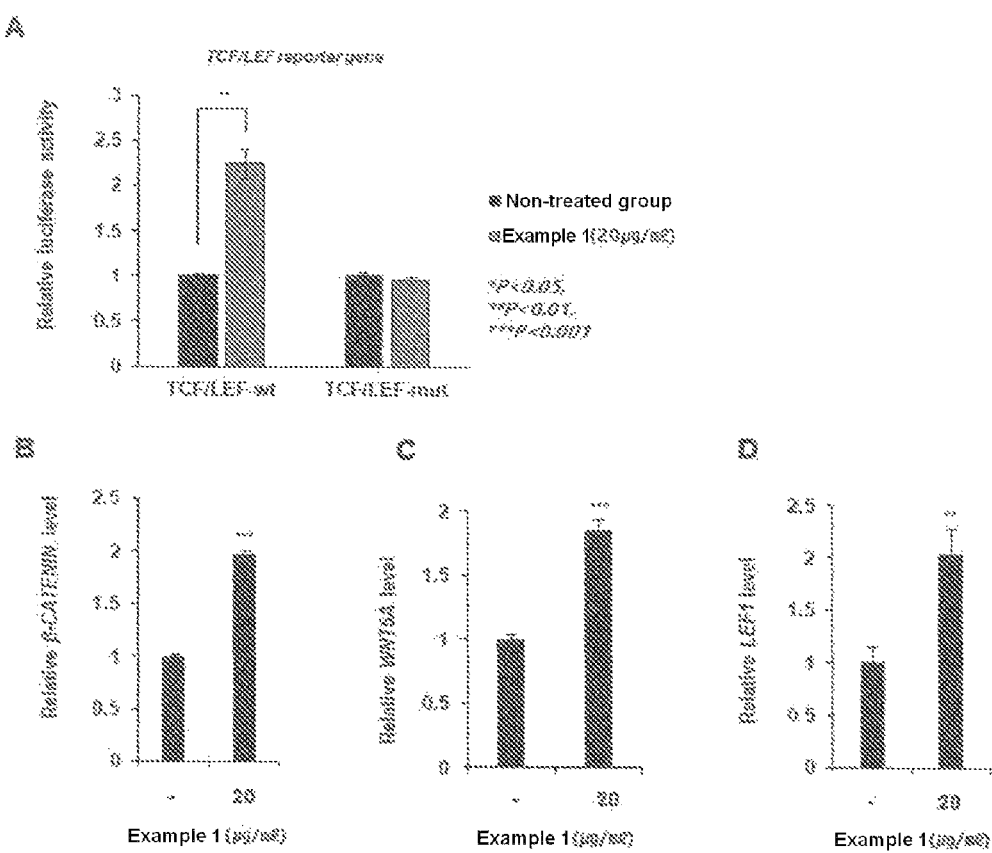
FIG. 5A shows assay results for TCF/LEF activity in HEK293 cells according to the treatment of Example 1 (ginsenoside Rg4) of the present disclosure and FIGS. 5B, 5C, and 5D show mRNA expression levels of β-catenin, WNT5A, and LEF1 in human hair follicle dermal papilla cells according to the treatment of Example 1 (ginsenoside Rg4) of the present disclosure.

With reference to FIG. 5, Example 1 increased the activation of TCF/LEF and the mRNA expression levels of β-catenin, WNT5A, and LEF1 two folds or more, compared to the non-treated group (control). Exhibiting the excellent effect of activating the Wnt/β-catenin signaling, therefore, Example 1 (ginsenoside Rg4) of the present disclosure can be used in a composition for promoting hair growth.

Experimental Example 3-3. Dermal Papilla Signature Gene Expression and Marker Associated with Hair Follicle Neogenesis Signature genes expressed in dermal papilla cells include genes coding for ALP (alkaline phosphatase) which significantly increase in expression level upon 3D culture and plays an important role in the neogenesis and growth of hair follicles, VCAN (versican) which plays an essential role in follicle neogenesis, BMP2 (bone morphogenetic protein 2) which is indispensable for dermal papilla cell functions, and FGF7 (fibroblast growth factor 7) which is involved in hair growth. After being applied to the 3D spheroid culture of human hair follicle dermal papilla cells in Experimental Example 1, the Examples of the present disclosure were examined for the effect of preventing hair loss and promoting hair growth by monitoring mRNA expression levels of ALPL, VCAN, BMP2, and FGF7.

The mRNA expression analysis of ALPL, VCAN, BMP2, and FGF7 was carried out in the same manner as for β-catenin, WNT5A, and LEF1 in Experimental Example 3-2, with the exception of using primer sets for ALPL, VCAN, FGF7, and BMP2 instead of those for β-catenin, WNT5A, and LEF1. The mRNA expression analysis data are depicted in FIGS. 6 and 7.

Figure 6:
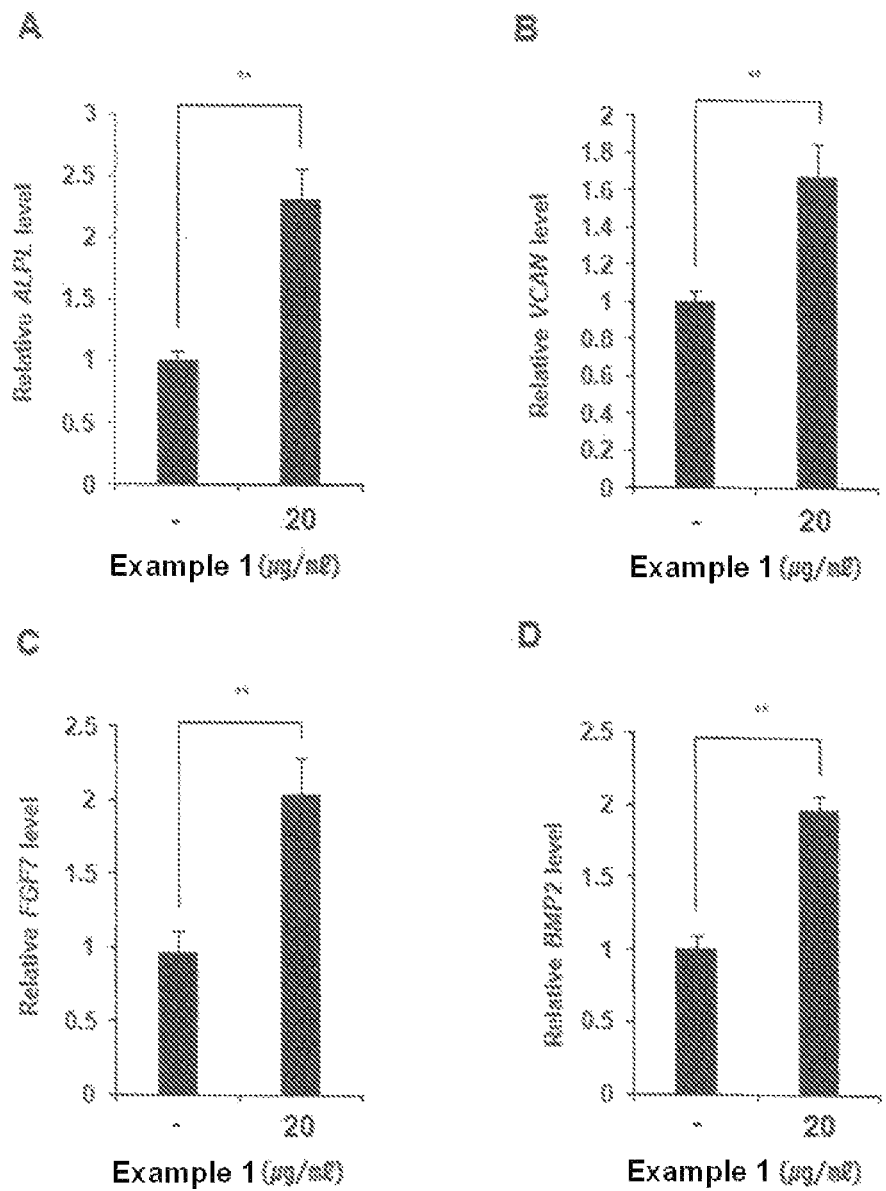
FIGS. 6A, 6B, 6C, and 6D show assay results for mRNA expression levels of ALPL, VCAN, FGF7, and BMP2 in human hair follicle dermal papilla cells cultured in a 3D pattern according to the treatment of Example 1 (ginsenoside Rg4) of the present disclosure.
Figure 7:
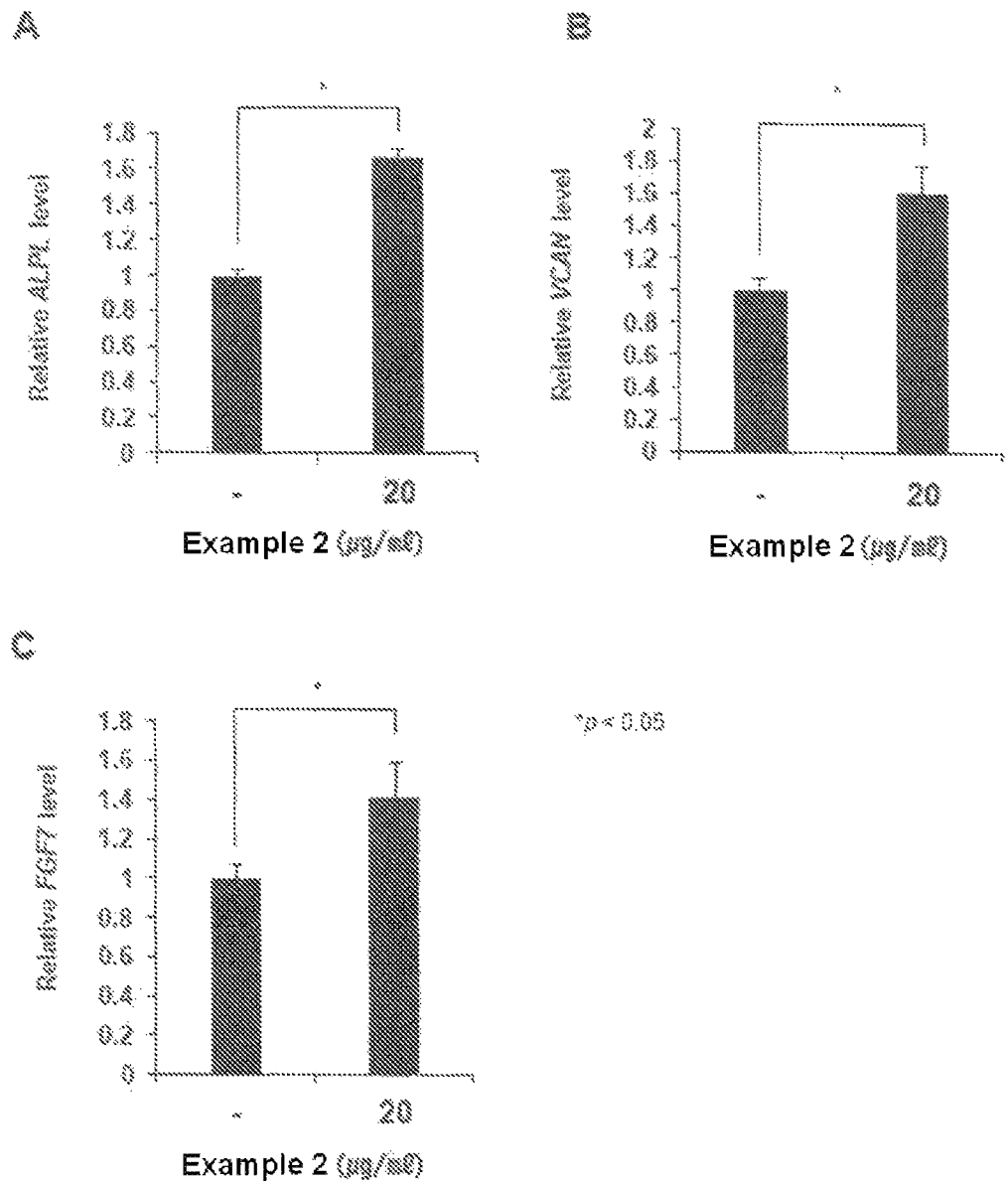
FIGS. 7A, 7B, and 7C show assay results for mRNA expression levels of ALPL, VCAN, and FGF7 in 3D cultured human hair follicle dermal papilla cells according to the treatment of Example 2 (Rgx 365) of the present disclosure.

Referring to FIGS. 6 and 7, the 3D spheroid culture of human hair follicle dermal papilla cells treated with Example 1 or 2 of the present disclosure increased in expression levels of all of ALPL, VCAN, BMP2, and FGF7, compared to the non-treated control, demonstrating that the Examples have an excellent effect of preventing hair loss and promoting hair growth.

From the result, it is understood that ginsenoside Rg4 or a mixture of ginsenosides Rg2, Rg4, Rg6, and Rh1 according to the present disclosure can be advantageously used in a composition for preventing hair loss or promoting hair growth.

Preparation Example 1: Hydrophilic Ointment Formulation

A hydrophilic ointment formulation was prepared by a typical method using the mixture (Rgx 365) of ginsenosides Rg2, Rg4, Rg6, and Rh1 of Example 2 of the present disclosure according to the composition listed in Table 1, below.

TABLE 1

| Material name | Content (% by weight) |
|---|---|
| Example 2 | 8.0 |
| White Vaseline | 35.0 |
| Stearyl alcohol | 30.0 |
| Ethyl (or methyl) p-oxybenzoate | Trace |
| Propylene glycol | 20.0 |
| Sodium lauryl sulfate | 3.4 |
| Propyl p-oxybenzoate | Trace |

Preparation Example 2: Preparation of Skin Lotion Formulation

A skin lotion formulation was prepared by a typical method using the mixture (Rgx 365) of ginsenosides Rg2, Rg4, Rg6, and Rh1 of Example 2 of the present disclosure according to the composition listed in Table 2, below.

TABLE 2

| Material name | Content (% by weight) |
|---|---|
| Example 2 | 4.0 |
| Butylene glycol | 3.5 |
| Glycerin | 2.5 |
| Polyoxyethylene hydrogenated castor oil | 0.1 |
| Ethanol | 2.5 |
| Betaine | 1.0 |
| Citric acid | 0.01 |
| Sodium citrate | 0.03 |
| Preservative | Suitable amount |
| Fragrance | Suitable amount |
| Purified water | to 100 |

Preparation Example 3: Preparation of Cream Formulation

A cream formulation was prepared by a typical method using the mixture (Rgx 365) of ginsenosides Rg2, Rg4, Rg6, and Rh1 of Example 2 of the present disclosure according to the composition listed in Table 3, below.

TABLE 3

| Material name | % by weight (w/w) |
|---|---|
| Example 2 | 7.0 |
| Cetostearyl alcohol | 3.0 |
| Self-emulsifying monostearic acid | 1.5 |
| Lipophilic monostearic acid | 1.5 |
| Bee wax | 0.5 |
| Liquid paraffin | 8.0 |
| Squalane | 7.0 |
| Isocetyl octanoate | 4.0 |
| Purified jojoba oil | 4.0 |
| Dimethyl siloxane | 0.3 |
| Sorbitan monostearate | 1.0 |
| Ethylene glycol monostearate | 1.2 |
| Glycerin | 6.0 |
| Propylene glycol | 4.0 |
| Betaine | 4.0 |
| Xanthan gum | 0.06 |
| Triethanolamine | 0.10 |
| Preservative | 0.25 |

TABLE 3-continued

| Material name | % by weight (w/w) |
|---|---|
| Fragrance | Suitable amount |
| Pigment | Suitable amount |
| Purified water | to 100 |

Preparation Example 4: Preparation of Health Function Food

Granules were prepared by mixing 20 g of Example 2 (ginsenoside Rg2, Rg4, Rg6, and Rh1 mixture, Rgx 365), a suitable amount of a vitamin complex, 70 μg of vitamin A acetate, 1.0 mg of vitamin E, 0.13 mg of vitamin B1, 0.15 mg of vitamin B2, 0.5 mg of vitamin B6, 0.2 μg of vitamin B12, 10 mg of vitamin C, 10 μg of biotin, 1.7 mg of nicotinamide, 50 μg of folic acid, 0.5 mg of calcium pantothenate, a suitable amount of an inorganic mixture, 1.75 mg of ferrous sulfate, 0.82 mg of zinc oxide, 25.3 mg of magnesium carbonate, 15 mg of potassium phosphate monobasic, 55 mg of calcium phosphate dibasic, 90 mg of potassium citrate, 100 mg of calcium carbonate, and 24.8 mg of magnesium chloride, and can be modified into various formulations. In addition, any modification may be imparted to the composition ratio of vitamin and mineral mixtures and the ingredients may be mixed according to typical preparation methods for health function foods.

Preparation Example 5: Preparation of Health Functional Beverage

A beverage was prepared by mixing 1 g of Example 2 of the present disclosure (ginsenoside Rg2, Rg4, Rg6, and Rh1 mixture, Rgx 365), 0.1 g of citric acid, 100 g of fructooligosaccharide, and 900 g of purified water, and stirring, heating, filtering, sterilizing, and refrigerating the mixture according to a typical beverage preparation method.

The invention claimed is:

1. A method for preventing hair loss or promoting hair growth in a subject, comprising administering to the subject in need thereof an effective amount of the pharmaceutical composition of ginsenoside Rg4 and pharmaceutically acceptable carriers, and wherein the pharmaceutical composition comprises 30-40% by weight of ginsenoside Rg4.

2. A method for preventing hair loss or promoting hair growth in a subject, comprising administering to the subject in need thereof an effective amount of the cosmetic composition of ginsenoside Rg4 and cosmetically acceptable carriers, and wherein the pharmaceutical composition comprises 30-40% by weight of ginsenoside Rg4.

3. A method for preventing hair loss or promoting hair growth in a subject, comprising administering to the subject in need thereof an effective amount of the health functional food of ginsenoside Rg4 and health-functionally acceptable carriers, and wherein the pharmaceutical composition comprises 30-40% by weight of ginsenoside Rg4.

4. The method of claim 1, wherein the active ingredient in the pharmaceutical composition further comprises ginsenosides Rg2, Rg6, and Rh1 as a mixture with the ginsenoside Rg4.

5. The method of claim 4, wherein the mixture comprises 35-45% by weight of ginsenoside Rg2, 10-20% by weight of ginsenoside Rg6, and 1-5% by weight of ginsenoside Rh1.

6. The method of claim 2, wherein the active ingredient in the cosmetic composition further comprises ginsenosides Rg2, Rg6, and Rh1 as a mixture with the ginsenoside Rg4.

7. The method of claim 6, wherein the mixture comprises 35-45% by weight of ginsenoside Rg2, 10-20% by weight of ginsenoside Rg6, and 1-5% by weight of ginsenoside Rh1.

8. The method of claim 3, wherein the active ingredient in the health functional food composition further comprises ginsenosides Rg2, Rg6, and Rh1 as a mixture with the ginsenoside Rg4.

9. The method of claim 8, wherein the mixture comprises 35-45% by weight of ginsenoside Rg2, 10-20% by weight of ginsenoside Rg6, and 1-5% by weight of ginsenoside Rh1.

* * * * *